(12) United States Patent
Piantoni et al.

(10) Patent No.: US 10,441,477 B2
(45) Date of Patent: Oct. 15, 2019

(54) PROCESS AND MACHINE FOR FORMING AN ABSORBENT SANITARY ARTICLE

(71) Applicant: GDM S.p.A., Bologna (IT)

(72) Inventors: Matteo Piantoni, Albino (IT); Valerio Soli, Bologna (IT)

(73) Assignee: GDM S.P.A., Bologna (IT)

( * ) Notice: Subject to any disclaimer, the term of this patent is extended or adjusted under 35 U.S.C. 154(b) by 98 days.

(21) Appl. No.: 15/112,939

(22) PCT Filed: Feb. 16, 2015

(86) PCT No.: PCT/IB2015/051137
§ 371 (c)(1),
(2) Date: Jul. 20, 2016

(87) PCT Pub. No.: WO2015/125059
PCT Pub. Date: Aug. 27, 2015

(65) Prior Publication Data
US 2016/0331597 A1    Nov. 17, 2016

(30) Foreign Application Priority Data

Feb. 18, 2014 (IT) .............................. BO2014A0077
Mar. 12, 2014 (IT) .............................. BO2014A0124

(51) Int. Cl.
*A61F 13/15* (2006.01)

(52) U.S. Cl.
CPC .. *A61F 13/15804* (2013.01); *A61F 13/15699* (2013.01); *A61F 13/15723* (2013.01);
(Continued)

(58) Field of Classification Search
CPC .......... A61F 13/15804; A61F 13/15699; A61F 13/15764; A61F 13/15739; A61F 13/15577
See application file for complete search history.

(56) References Cited

U.S. PATENT DOCUMENTS 4,557,777 A   12/1985  Sabee
5,900,109 A    5/1999  Sanders et al.
(Continued)

FOREIGN PATENT DOCUMENTS

CN   101257874 A   9/2008
CN   101541286     9/2009
(Continued)

OTHER PUBLICATIONS

International Search Report and Written Opinion dated Jun. 11, 2015 for counterpart PCT application No. PCT/IB2015/051137.
(Continued)

*Primary Examiner* — Mark A Osele
*Assistant Examiner* — Christopher C Caillouet
(74) *Attorney, Agent, or Firm* — Shuttleworth & Ingersoll, PLC; Timothy J. Klima

(57) ABSTRACT

A process for forming an absorbent sanitary article of the type including a pad having a direction of main extension, including a step of at least one absorbent core of the absorbent article by layering a corresponding composite web, a step of preparing a succession of hollows in the composite web obtained by removing for each hollow a corresponding portion of the composite web and a step of applying the portions removed on the composite web.

11 Claims, 3 Drawing Sheets

(52) U.S. Cl.
CPC .. *A61F 13/15739* (2013.01); *A61F 13/15764* (2013.01); *A61F 2013/15821* (2013.01)

(56) References Cited

U.S. PATENT DOCUMENTS

| | | | |
|---|---|---|---|
| 6,369,291 | B1* | 4/2002 | Uchimoto |
| 7,766,887 | B2 | 8/2010 | Burns et al. |
| 8,057,620 | B2 | 11/2011 | Perego et al. |
| 8,282,616 | B2 | 10/2012 | Lehto et al. |
| 10,259,185 | B2 | 8/2019 | Rosani et al. |
| 2003/0131943 | A1 | 7/2003 | Frederisy |
| 2005/0020992 | A1 | 1/2005 | Van Gompel et al. |
| 2005/0103436 | A1* | 5/2005 | Otsubo |
| 2008/0114319 | A1 | 5/2008 | Burns et al. |
| 2010/0258242 | A1 | 10/2010 | Burns, Jr. et al. |
| 2011/0112500 | A1 | 5/2011 | Wenzel et al. |
| 2011/0125122 | A1 | 5/2011 | Thorson et al. |
| 2011/0247199 | A1 | 10/2011 | LaVon et al. |
| 2014/0024514 | A1 | 1/2014 | Rosani et al. |

FOREIGN PATENT DOCUMENTS

| | | |
|---|---|---|
| CN | 101568314 A | 10/2009 |
| CN | 103561701 | 2/2014 |
| JP | H05123361 A | 5/1993 |
| JP | H06178793 A | 6/1994 |
| JP | 2003339750 A | 12/2003 |
| JP | 2010508944 A | 3/2010 |
| JP | 2012501765 A | 1/2012 |
| JP | 2013523331 A | 6/2013 |
| JP | 2014510591 A | 5/2014 |

OTHER PUBLICATIONS

Japanese Office Action dated Feb. 15, 2019 for counterpart Japanese Patent Application No. 2016-552565.
Chinese Office Action dated Jan. 4, 2019 for counterpart Chinese Patent Application No. CN201580009057.
Chinese Search Report dated Dec. 26, 2018 from counterpart Chinese Patent Application No. CN201580009057.
Chinese Office Action dated Jun. 11, 2019 from counterpart Chinese Patent Application No. CN201580009057.

* cited by examiner

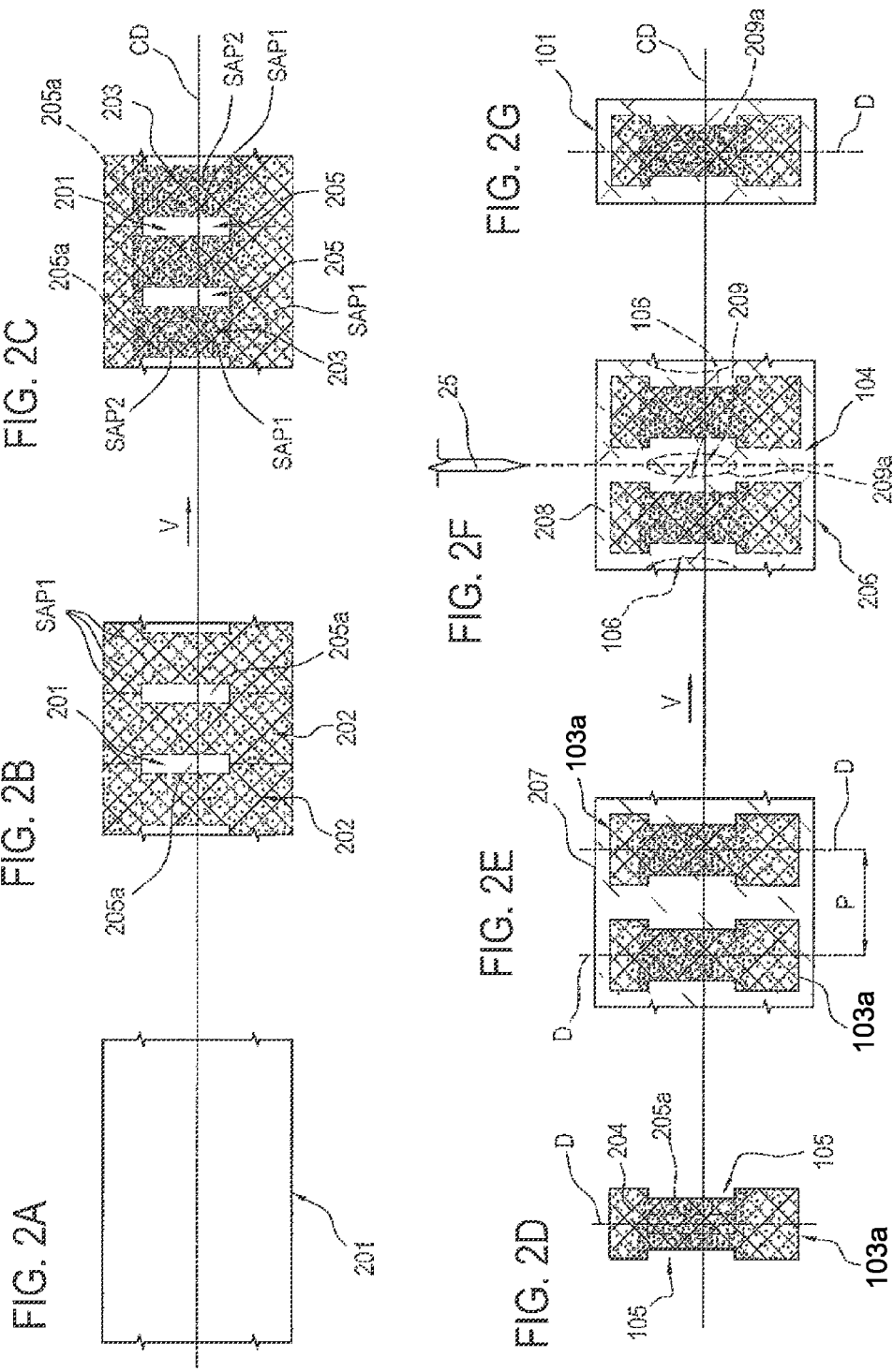

PROCESS AND MACHINE FOR FORMING AN ABSORBENT SANITARY ARTICLE

This application is the National Phase of International Application PCT/IB2015/051137 filed Feb. 16, 2015 which designated the U.S. and that International Application was published under PCT Article 21(2) in English.

This application claims priority to Italian Patent Application No. BO2014A000077 filed Feb. 18, 2014, and Italian Patent Application No. BO2014A000124 filed Mar. 12, 2014. Both applications are incorporated by reference herein.

TECHNICAL FIELD

This invention relates to a process and a machine for forming an absorbent sanitary article.

BACKGROUND ART

In the field of machines for forming absorbent sanitary articles, such as nappies for babies, sanitary towels or the like, there are a plurality of prior art solutions depending on the articles which are to be made.

The prior art absorbent sanitary articles comprise an absorbent padding or pad which is normally enclosed between a permeable inner layer of non-woven fabric and an impermeable outer layer of polyethylene.

Usually, the absorbent pads for absorbent sanitary articles are relatively thick and are obtained by cutting into lengths a continuous web comprising an aggregate of absorbent material.

The lengths thus obtained are inserted in a continuous composite web comprising, externally, the above-mentioned inner layer and the above-mentioned outer layer in the form of respective webs.

However, the machines for making the absorbent articles have significant drawbacks.

Firstly, these machines have large dimensions due to the production of the entire absorbent sanitary article by superposing successive layers extending in the form of a web.

The prior art machines are also relative slow and not very versatile since they do not allow modifications to be easily made based on changes to the features of the finished product.

DISCLOSURE OF THE INVENTION

In this context, the main purpose of this invention is to provide a process and a machine for forming absorbent sanitary articles which overcome the above-mentioned drawbacks.

One aim of this invention is to provide a process for forming absorbent sanitary articles which is particularly effective and fast.

Another aim of this invention is to provide a machine for making absorbent sanitary articles which is more versatile than the prior art solutions.

The technical purpose and aims specified are substantially achieved by a process for forming an absorbent sanitary article comprising technical features as disclosed herein and by a machine for forming an absorbent sanitary article comprising technical features as disclosed herein.

BRIEF DESCRIPTION OF DRAWINGS

Further features and advantages of this invention are more apparent in the detailed description below, with reference to a preferred, non-limiting embodiment of a machine and a process for forming absorbent sanitary articles as illustrated in the accompanying drawings, in which:

FIGS. 2A to 2L schematically illustrate a sequence of steps of the forming process according to this invention.

DETAILED DESCRIPTION OF THE PREFERRED EMBODIMENTS OF THE INVENTION

Figure 1:
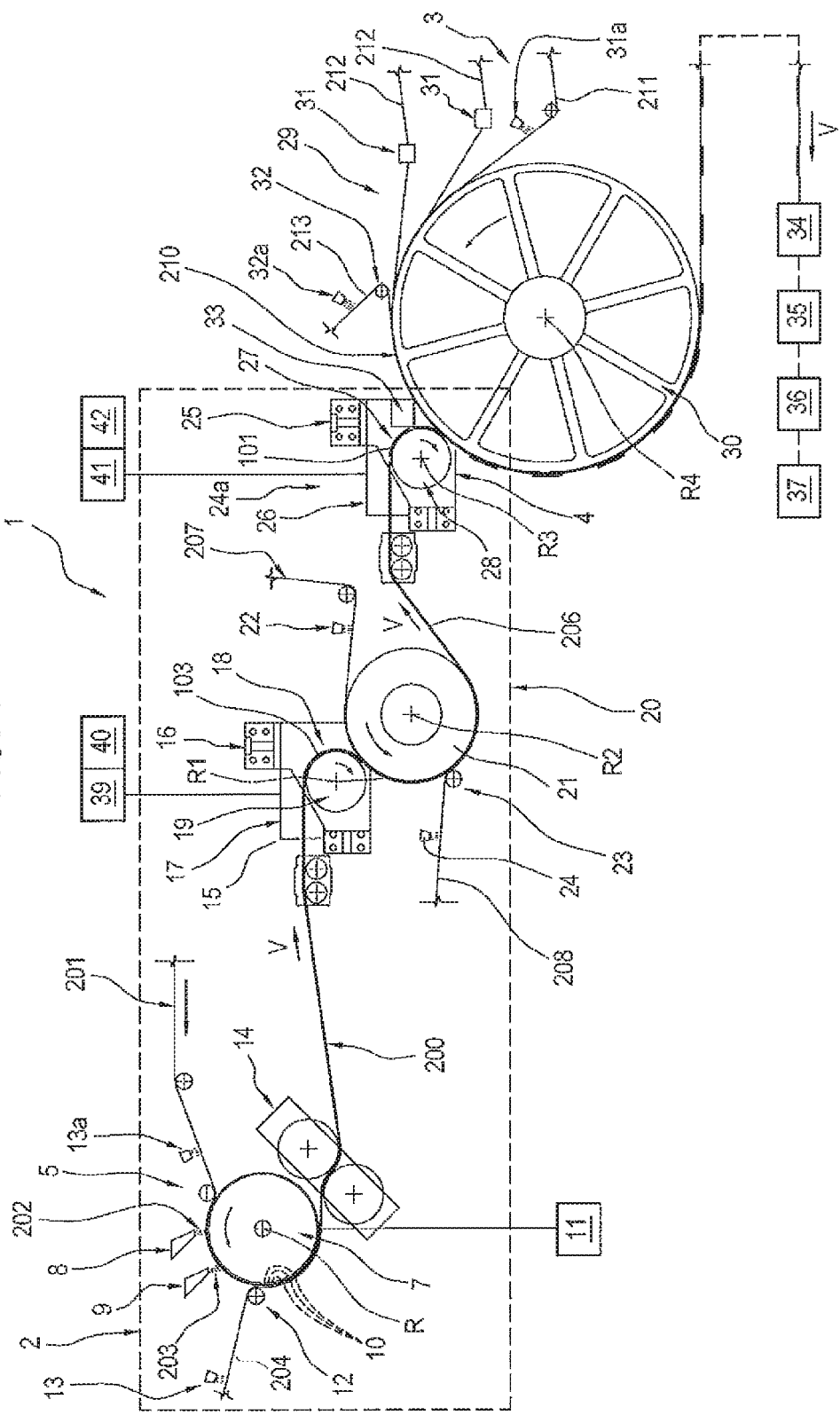
FIG. 1 illustrates a schematic side view partly in blocks and with some parts cut away for greater clarity of a machine for forming an absorbent sanitary article.

With reference to the accompanying drawings, the numeral 1 denotes a machine for forming absorbent sanitary articles 100.

The generic article 100 comprises a pad 101, having a main direction of extension D, and a frame 102 supporting the pad 101.

The pad 101 comprises an absorbent core 103 and a coating or cover 104 of the absorbent core 103 both having the same main direction of extension D as the pad 101.

The machine 1 comprises a unit 2 for forming the pad 101 for positioning the pads 101 as separate elements, as described in more detail below.

The machine 1 comprises a unit 3 for forming the frame 102 of the article 100. As explained below, the frames 102 are made in the form of a continuous composite web on which the pads 101, suitably spaced, are applied, for example glued.

The machine 1 comprises a unit 4 for applying the pad 101 to the frame 102, in particular to the above-mentioned composite web defined, in practice, by a series of frames 102 defining the composite web.

The articles 100 are defined by cutting into lengths the above-mentioned composite web once the pads 101 are attached on it.

The unit 2 for forming the pads 101 comprises a station 5 for forming a composite web 200 from which the absorbent cores 103 are made.

In the preferred embodiment illustrated, the station 5 comprises a drum 7 for forming and rotatably feeding about an axis R in an anticlockwise direction in the example illustrated.

The drum 7 is designed for feeding a first supporting web 201 for forming the composite web 200.

The web 201 is fed along a feed direction CD in a feed direction V, as schematically illustrated in FIG. 2A.

The feed direction CD, which corresponds to a main direction of extension of the web 201, is transversal to the main direction of extension D of the pads 101 and of the absorbent cores 103.

In other words, as described below, the machine 1 is preferably designed to operate with a method known in the trade for the manufacturing of absorbent sanitary articles as "cross direction" which allows a greater number of absorbent articles to be obtained with the same speed relative to a machine operating in the so-called "machine direction" method.

The station 5 for forming absorbent cores 103 comprises a unit 8 for positioning on the forming drum 7, in particular on the web 201, a spread 202 of absorbent material, for example absorbent SAP1 polymeric material, as illustrated schematically in FIG. 2B.

Preferably, as illustrated in FIG. 1, the station 5 comprises a second unit 9 for positioning on the forming drum 7, in particular on the web 201, a second spread 203 of absorbent material, for example absorbent SAP2 polymeric material, as also schematically illustrated in FIG. 2C.

The second unit 9 is located downstream of the first unit 8 in the feed direction of the web 201 and the second spread 203 is at least partly positioned on the first spread 202.

Preferably, the station 5, in particular the drum 7, comprises means for positioning absorbent material spread on the supporting web 201 according to a predetermined model.

Advantageously, the positioning means also contribute to the retaining and feeding of the web 201.

In a preferred embodiment, so as to retain and feed the first web 201 along the feed direction CD, the drum 7 has a plurality of seats 10 positioned along its periphery, more specifically, on the peripheral surface of the drum 7, and a suction system, schematically illustrated with a block labelled 11, associated with the seats 10 and designed to generate a negative pressure at the seats 10 such as to retain inside each of them a portion of the first web 201.

The "held-down" portion defines a zone (or pocket) for receiving the absorbent material SAP1 and/or SAP2.

Advantageously, the suction system 11 is sized to generate, at each seat 10, a negative pressure such as to hold in the respective pocket the absorbent polymeric material SAP1 and/or SAP2.

More specifically, the negative pressure is such that all the absorbent polymer material SAP1 and/or SAP2 interposed between two adjacent seats 10 is transported inside the respective pockets.

In that way, there are zones on the first web 201 free of the absorbent material, that is to say, the absorbent material is spread according to a predetermined model determined by the positioning and/or of the shapes of the seats 10 at which the absorbent material is positioned and retained.

Preferably, as explained in more detail below, the predetermined model for positioning the absorbent material is such that the above-mentioned zones free of absorbent material comprise zones of sealing a composite web comprising the web 201.

In other words, the composite web comprising the web 201 will comprise zones or lines for sealing free from the absorbent material.

Preferably, as explained in more detail below, the predetermined model for positioning the absorbent material is such that the above-mentioned zones free of absorbent material comprise zones for cutting the composite web comprising the web 201

In other words, the composite web comprising the web 201 will comprise zones or lines for cutting free from the absorbent material.

The station 5 comprises a system 12 for applying a second web 204 on the first web 201 and on the absorbent material located on the web 201.

The application system 12 comprises a system for unwinding the web 204, substantially of known type and not described, and, preferably, a device 13 for dispensing adhesive to place the adhesive on a face of the web 204 designed to enter into contact with the web 201 to form in its entirety the composite web 200.

In a preferred embodiment, the station 5 comprises a second device 13a for dispensing adhesive to place adhesive on a face of the web 201 designed to receive the absorbent material and to enter into contact with the web 204 to form in its entirety the composite web 200.

The adhesive provided on the web 204 and/or on the web 201 determines a greater stability of the absorbent material between the webs 201, 204.

Downstream of the drum 7 in the feed direction V of the web 200, comprising the web 201, the absorbent material SAP1 and/or SAP2 and the web 204, the station 5 for forming the web 200 comprises a sealing unit, preferably of substantially known type, not described in detail and schematically illustrated with a block 14, operating on the first and on the second web 201, 204 to seal them together according to a predetermined sealing model.

It should be noted that the sealing unit 14, is preferably configured to couple the web 204 to the web 201 at the above-mentioned zones free from the absorbent material.

Advantageously, the sealing unit 14 also acts as laminator of the composite web 200.

The unit 2 forming the pad comprises a cutting station 15, positioned downstream of the sealing unit 14 in the feed direction V of the web 200, wherein the composite web 200 is cut into a plurality of first lengths of absorbent core 103a, one of which is illustrated schematically in FIG. 2D, each first length of absorbent core 103a forming a corresponding absorbent core 103; for simplicity, the first lengths 103a of the first web 200, that is to say, the sections of the first web 200 corresponding to the first lengths 103a, are denoted by the reference 103a.

The station 15 comprises a cutting device 16 operating along the feed direction CD for cutting the web 200 into lengths 103a.

The device 16 operates along a cutting direction D1 transversal to the feed direction of the web 200.

In a preferred embodiment, the cutting station comprises a device, schematically illustrated with a block 17, for shaping the absorbent core in such a way as to shape the absorbent core into a preferred shape most comfortable for a generic wearer.

Each absorbent core 103 is shaped, forming in the absorbent cores 103 openings 105 substantially at the crotch of the wearer.

The shaping device 17 is located upstream of the device 16 for cutting into lengths in the feed direction V of the web 200.

The device 17, in particular, operates on the web 200 for preparing a succession of hollows 205 in the web.

In the preferred embodiment illustrated, to which express reference will hereinafter be made but without thereby limiting the scope of the invention, the hollows 205 are in the form of holes 205 made in the web 200.

More specifically, the shaping device 17 removes parts or portions 205a of the web 200 forming in the web the holes 205.

As illustrated schematically for example in FIG. 2C, in the preferred embodiment, each hole 205 touches adjacent lengths 103a.

In alternative embodiments not illustrated, wherein, for example, the web 200 advances in a direction parallel to the relative main direction of extension and to the main direction D of extension D of the pads 101 and of the absorbent cores 103, the hollows 205 are in the form of corresponding notches.

In practice, as will become clearer as this description continues, the preparation of the hollows or holes 205 in the web 200 occurs before applying the pad 101 on the frame 102.

Preferably, in order to optimize the work of the cutting device 16 and/or of the shaping device 17, the above-mentioned drum 7 is shaped, as already mentioned, in such a way that at the transversal cutting lines there are the above-mentioned zones free of absorbent material.

In a preferred embodiment, the machine 1, in particular the cutting station 15, comprises a device for gripping and positioning the parts 205a removed from the web 200, schematically represented as a block 39.

The device 39 is configured to pick up a portion 205a from the web 200 and position it on a length of the web 200 corresponding to a length 103a.

Preferably, each portion 205a is positioned on a corresponding length of the web 200 with its main direction of extension D oriented like the main direction of extension D of the pad 101.

Preferably, each portion 205a is positioned on a length of the web 200 corresponding to a length 103a at the crotch of the generic wearer.

The machine 1, in particular the station 15, comprises a device 40 for dispensing adhesive for applying the adhesive on the web 200 at a zone for gluing the portions 205a.

In an alternative embodiment, the device 40 applies the adhesive on the portions 205a.

In a preferred embodiment, in order to optimize the work of the shaping device 17, the above-mentioned drum 7 is shaped, as already mentioned, in such a way that at the holes 205 there are the above-mentioned zones free of absorbent material.

In other words, in an embodiment, the parts 205a of web to be removed are free of absorbent material.

In an alternative embodiment, the absorbent material is also placed in the portions 205a the web 200.

Advantageously, if the portions 205a are free of absorbent material and are positioned on the web 200 they will define in the corresponding article 100 an additional layer for acquisition and distribution of the liquid, known in the trade by the acronym ADL (Acquisition Distribution Layer).

In this way the cutting device 16 and/or the shaping device 17 act only on the webs 201 and 204 without touching, during cutting, absorbent material.

Advantageously, if the portions 205a also comprise absorbent material and are positioned on the web 200 they contribute to the definition of a suitable distribution of absorbent material in the absorbent core 103.

In a preferred embodiment, the web 201 is made from a web of non-woven fabric, whilst the web 204 is a web of non-woven fabric with open fibre of the type known with the name "loft" or "high loft".

The unit 2 forming the pads comprises, positioned downstream of the devices 16 and 17, a system 18 for feeding the lengths 103a.

The feed system 18 comprises for example a suction drum 19, rotatable about an axis of rotation R1, of substantially known type and not described in detail, rotatable in a clockwise direction in the example illustrated, which retains and feeds the lengths 103a along the feed direction CD in the feed direction V.

Preferably, the system 18 also comprises a system for spacing the lengths 103a in such a way as to make a succession of lengths 103a spaced by a predetermined interval P, as shown in FIG. 2E.

The system of spacing is preferably incorporated in the above-mentioned drum 19 for retaining and feeding the lengths 103a.

In the preferred embodiment illustrated, the unit 2 for forming the pads 101 comprises a station 20 for forming a second composite web 206 positioned downstream of the station 5 according to the feed direction V of the lengths 103a and in communication with the feed and spacing system 18 for receiving the lengths 103a.

In the preferred embodiment illustrated, the station 5 comprises a drum 21 for forming and rotatably feeding about an axis R2 in an anticlockwise direction in the example illustrated.

The drum 21, preferably of the suction type, is designed for feeding a supporting web 207 used for forming the composite web 206 and substantially tangential to the drum 19 for receiving from it the lengths 103a suitably spaced.

The web 207 is fed along the feed direction CD in such a way that the lengths 103a are positioned on the web 207 with its main direction of extension D transversal to the main direction of extension and feeding of the web 207.

The station 20 comprises a device 22 for dispensing adhesive to place adhesive on one face of the web 207 designed to receive the lengths 103a.

In that way, the lengths 103a, once positioned on the web 207, remain attached to it, in particular due both to a suction action of the drum 21 and the presence of the adhesive spread from the dispensing device 22.

The station 20 comprises a system 23 for applying a web 208 on the web 207 and on the lengths 103a positioned on the web 207.

The system 23 for applying the web 208 comprises a system for unwinding the web 208, of substantially known type, schematically illustrated with a corresponding roller and, preferably, a device 24 for dispensing adhesive to place adhesive on one face of the web 208 designed to enter into contact with the web 207 and with the lengths 103a to form in its entirety the composite web 206, a length of which is illustrated schematically in FIG. 2F.

Preferably, the system 23 defines a device for laminating the web 206.

The unit 2 for forming the pads 101 comprises a cutting station 24a, positioned downstream of the system 23 for applying the web 208 in the feed direction V of the web 203, wherein the composite web 206 is cut into a plurality of lengths, each defining a corresponding pad 101 and schematically illustrated in FIG. 2G.

For simplicity, the lengths of the web 206, that is to say, the sections of the second web 206 corresponding to the lengths, are denoted by the same reference 101 as the pads of the article 100.

The station 24a comprises a cutting device 25 operating along the feed direction CD for cutting the web 206 into lengths 101.

The device 25 operates along a cutting direction D1 transversal to the feed direction CD of the web 200.

Each pad 101 is in practice formed by an absorbent core 103 equipped with the outer cover 104 made from the webs 207 and 208.

In a preferred embodiment, the web 207 comprises a polyethylene film whilst the web 208 is made of non-woven fabric.

In a preferred embodiment, the cutting station 24a comprises a device, schematically illustrated with a block 26, for shaping the cover 104 in such a way as to shape the cover 104 into a preferred shape most comfortable for a generic wearer, in particular forming in the coverings 104 the openings 106, illustrated with a dashed line, substantially at the crotch of the wearer, that is to say, at the openings 105 the absorbent core 103.

The shaping device 26 is located upstream of the device 25 for cutting into lengths in the feed direction V of the web 206.

The device 26, in particular, operates on the web 206 for preparing a succession of hollows 209 in the web.

In the preferred embodiment illustrated, to which express reference will hereinafter be made but without thereby limiting the scope of the invention, the hollows 209 are in the form of holes 209 made in the web 206.

More specifically, the shaping device 26 removes parts or portions 209a of the web 206 forming in the web the holes 209.

As illustrated schematically in FIG. 2F, in the preferred embodiment, each hole 209 touches adjacent lengths 101.

In alternative embodiments not illustrated, wherein, for example, the web 206 advances in a direction parallel to the relative main direction of extension and to the main direction D of extension D of the pads 101, the hollows 209 are in the form of corresponding notches.

In practice, as will become clearer as this description continues, the preparation of the hollows or holes 209 in the web 206 occurs before applying the pad 101 on the frame 102.

In a preferred embodiment, the machine 1, in particular the cutting station 24a, comprises a device for gripping and positioning the parts 209a removed from the web 206, schematically represented as a block 41.

The device 41 is configured to pick up a portion 209a from the web 206 and position it on a length of the web 206 corresponding to a pad 101.

Preferably, each portion 209a is positioned on a corresponding length of the web 206 with its main direction of extension D oriented like the main direction of extension D of the pad 101.

Preferably, each portion 209a is positioned on a length of the web 200 corresponding to a pad 101 at the crotch of the generic wearer.

The machine 1, in particular the station 24a, comprises a device 42 for dispensing adhesive for applying the adhesive on the web 206 at a zone for gluing the portions 209a.

In an alternative embodiment, the device 42 applies the adhesive on the portions 209a.

Advantageously, the portions 209a positioned on the web 206 form in the corresponding pad 101 an additional layer for acquisition and distribution of the liquid.

The unit 2 for forming the pads comprises, positioned downstream of the device 25, a system 27 for feeding the lengths 101.

The feed system 27, comprising, for example, a suction drum 28 rotatable about an axis of rotation R3, in a clockwise direction in the example illustrated, of substantially known type and not described in detail, which retains and feeds the lengths 101 in the feed direction V.

Figure 2H:
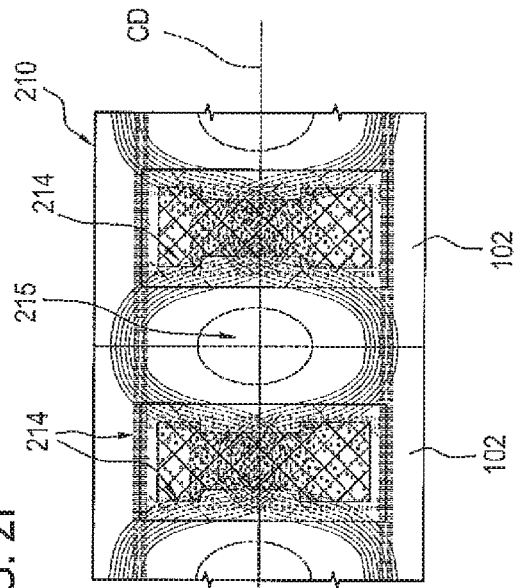

Preferably, the system 27 also comprises a system for spacing the lengths 101 in such a way as to make a succession of lengths 101 spaced by a predetermined interval P1, as schematically illustrated in FIG. 2H.

The spacing system is preferably integrated in the drum 28 for retaining and feeding the lengths 101.

The unit 3 for forming the frame comprises a station 29 for forming a composite web 210 from which the frames 102 are made.

The station 29 is preferably located downstream of the unit for forming the pads 101 and in particular of the drum 28 for receiving from the station the lengths 101, as will be explained below.

The station 29 comprises a drum 30 for forming and feeding rotatably about an axis R4.

The drum 30, preferably of the suction type, is set up for feeding a supporting web 211 designed for forming the composite web 210 and rotates, in the example illustrated, in an anticlockwise direction.

The station 29 comprises a plurality of systems 31 for positioning elastic wires 212 on the web 211 according to a predetermined arrangement.

Figure 2I:
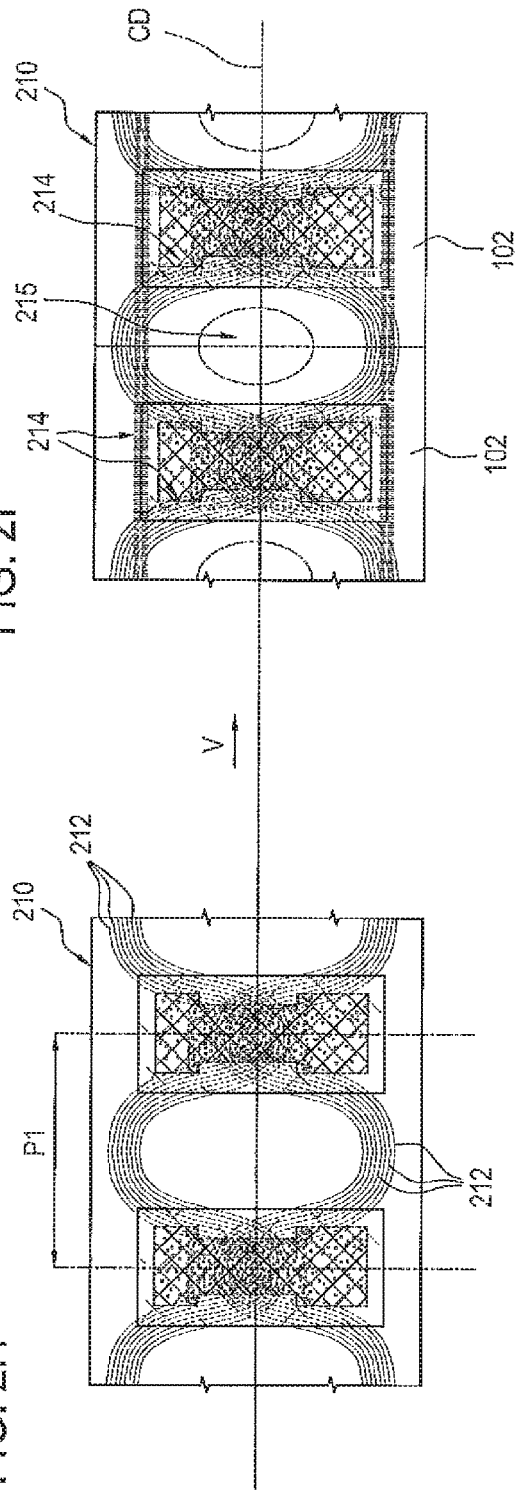
Figure 2L:
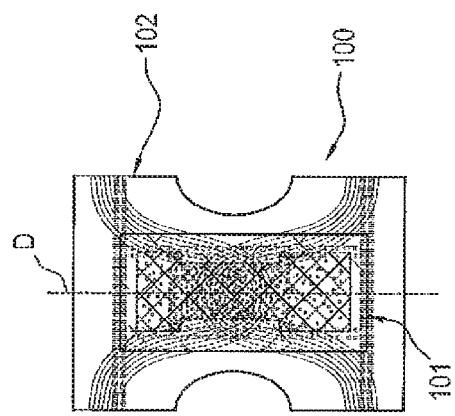

For example, the layout comprises a sinusoidal positioning as schematically illustrated in FIGS. 2H, 2I and 2L and substantially known.

Upstream of the systems 31 for placing the elastic wires 212 in the direction of rotation of the drum 30 the station 29 for forming the web 210 comprises a system 31 for applying adhesive on the web 211 for retaining the elastic wires 212 on the web 211.

Preferably, the application system 31 places the adhesive on the web substantially according to the predetermined arrangement for installing the elastic wires 212.

The station 29 for forming the web 210 comprises, positioned downstream of the systems 31 for placing the elastic wires 212 according to the direction of rotation of the drum 30, a system 32 for applying a web 213 on the web 211 and on the elastic wires 212 positioned on the web 211.

The web 211, the elastic wires 212 and the web 213 define the composite web 210 which constitutes in practice a continuous succession of frames 102.

The system 32 for applying the web 213 comprises a system for unwinding the web 208, of substantially known type, schematically illustrated with a corresponding roller and, preferably, a device 32a for dispensing adhesive to place adhesive on one face of the web 213 designed to enter into contact with the web 211 and with the elastic wires 212.

The drum 30 is substantially tangential, downstream of the system 32 for applying the web 213 in the direction of rotation of the drum 30, to the above-mentioned drum 28 to receive from it, as already mentioned, the lengths 101 suitably spaced.

The web 210 and the lengths 101 are fed in such a way that the lengths 101 are positioned on the web 210 with the main direction of extension D transversal to the main direction of extension and feed of the web 210.

In practice, the drum 28 forms part of the above-mentioned unit 4 for applying the pads 101 to the frame 102 in particular to the web 210.

The application unit 4 also comprises a device 33 for dispensing adhesive for applying an adhesive on the pads 101 fed by the drum 28, in particular on a face of each pad 101 opposite a face of the pad 101 by which the pad 101 is retained by the drum 28.

In that way, the pads 101 are provided with adhesive which allows the connection with the web 210.

In other words, the adhesive necessary for joining the pads 101 to the web 210 is placed on the pads 101 fed by the drum 28.

The machine 1 comprises, positioned downstream of the drum 30 in the feed direction V of the web 210 provided with the pads 101, a device, of substantially known type and schematically represented as a block 34, for application of elastic bands 214 preferably located substantially at the pads 101.

The elastic bands 214 define in the article 100 containment barriers of substantially known type.

The machine 1 comprises, positioned downstream of the device 32 in the feed direction V of the web 210, a station 35 for shaping the web 210, to form in it a succession of holes 215 at the openings 105 and 106 and a station 36 for cutting the web 210 into lengths 100, each defining a corresponding absorbent article.

Downstream of the station 36, the machine comprises a station 37 for folding and sealing each length 100 to form corresponding absorbent articles 100 of the type known with the name "pull up", not illustrated.

The station 37 is of substantially known type and not described further.

A process for forming an absorbent sanitary article 100 of the above-mentioned type comprises a step of forming the pads 101 of the absorbent article by layering a composite web, in particular by making the composite web 206, in the forming unit 2.

The process comprises a step of forming the frames 102 of the absorbent article 100 by layering a further composite web, in particular by making the composite web 210, in the unit 3.

The process comprises a step of applying the pads 101 to the frames 102, in particular a step of applying the pads 101 to the web 210.

The step of forming the pads 101 comprises a step of making the absorbent cores 103 by layering a corresponding composite web, in particular by making the composite web 200.

The step of making the absorbent cores 103 comprises a step of shaping the absorbent cores 103, in particular by making the holes 205 in the web 200 by removing the portions 205a.

The web 200 is preferably made by feeding the web 201 on the drum 7, placing on the web 201 the spread 202 of absorbent material and preferably the second spread 203 of absorbent material at least partly on the first, in such a way as to achieve in the article 100 different absorption capacities, that is to say, zones of different absorption capacities according to the spreads 202 and 203.

Each spread 202 and 203 is placed according to a corresponding placing model and the web 204 is applied to the web 201, preferably conveniently glued using adhesive, applied to the web 202 and/or to the web 203, to define the web 200.

Moreover, in an embodiment, the spread models preferably do not have absorbent material placed at the zones in which holes are to made, that is to say, at the above-mentioned holes 205.

In a preferred embodiment, the process comprises a step of applying the portions 205a removed on a corresponding length 103a to define the above-mentioned acquisition and distribution layer or a desired distribution of absorbent material if in the portions 205a removed there is absorbent material.

The step of making the absorbent cores 103 comprises a step of cutting the composite web 200 into lengths 103a, each forming an absorbent core.

The step of forming the pads comprises a step of covering the absorbent cores 103 with the outer cover 104 by making the composite web 206 comprising, as the intermediate layer, the lengths 103a. In practice, the lengths 103a define, in the web 206, an intermediate layer, in the middle of the lengths 207 and 208.

The lengths 103a are arranged in the web 206 suitably spaced along the feed direction CD, that is to say, along the main direction of extension of the web 206.

The web 206 is made by feeding the web 207 on the drum 21, placing the lengths 103a on the web 207 suitably spaced and applying the web 208 on the web 207, preferably also providing connecting adhesive on the web 208.

In a preferred embodiment, the step of making the pads 101 comprises a step of shaping the pads 101, in particular by making the holes 209 in the web 206 by removing the portions 209a.

In a preferred embodiment, the process comprises a step of applying the portions 209a removed on a corresponding pad 101 on the web 206 to form an above-mentioned layer for acquisition and distribution of liquid.

The step of forming the pads 101 comprises a step of cutting the web 206 into lengths, each forming a corresponding pad of an absorbent sanitary article 100.

The web 206 is cut in the cutting direction transversal to the feed direction of the web 206.

The step of forming the frames 102 is accomplished by making the composite web 210 formed by the webs 211, 213 and by the elastic wires 212.

More specifically, the web 210 is layered by feeding the web 211 on the drum 30, placing on the web 211 the elastic wires 212, having conveniently spread adhesive on the web 211, preferably substantially corresponding with the arrangement for positioning the wires 212. The web 210 is finished with the application of the web 213 on the web 211 and on the wires elastic 212.

The separate pads 101 are then glued, suitably spaced, on the web 210.

The web 210 with the pads 101 is then provided with the elastic bands 214 shaped and cut to form lengths 100 substantially corresponding to the absorbent articles 100.

The lengths 100 are then folded and sealed to obtain the so-called pull-up absorbent sanitary articles.

In light of the above, a preferred embodiment of an absorbent sanitary article 100, preferably made with the process and the machine described above, comprises the separate pad 101 supported, that is, glued to the frame 102.

The pad 101 comprises the absorbent core 103 and the cover 104 and is glued to the frame 102 using the cover 104.

The absorbent core 103 comprises a layer of non-woven fabric, preferably obtained from the web 201, on which is placed the absorbent material SAP1 and/or SAP2.

Above the absorbent material and above the layer of non-woven fabric there is a layer of open fibre material, preferably of the high loft type, preferably obtained from the web 204, sealed, at least partly, to the non-woven fabric layer.

The layer of non-woven fabric and the layer of loft or high loft material are sealed in accordance with the above-mentioned sealing model which preferably defines cells for containing the absorbent material.

The absorbent core 103 thus defined is inserted in the cover 104 which comprises, preferably, a layer of polyethylene and a layer of non-woven fabric between which is positioned the absorbent core 103.

The layer of polyethylene is preferably obtained from the web 207 whilst the layer of non-woven fabric of the cover 104 is obtained from the web 208.

In the preferred embodiment, the layer of non-woven fabric of the absorbent core 103 is put into contact with the layer of polyethylene of the cover 104.

The layer of loft or high loft material of the absorbent core 103 is, on the other hand, positioned in contact with the layer of non-woven fabric of the cover 104.

The pad 101 is preferably attached to the frame 101 through the layer of polyethylene which also forms an impermeable barrier of the absorbent sanitary article 100.

The invention described brings important advantages. More specifically, the making of the absorbent cores, the pads and the frames by layering separate corresponding composite webs, the lengths of which are suitably associated, allows a good versatility of the machine since individual forming stations or units can be replaced or modified as necessary.

The invention claimed is:

1. A process for forming an absorbent sanitary article comprising a pad having a direction of main extension and a frame for supporting the pad, the process comprising:
   a step of forming a frame of the absorbent sanitary article by layering a first composite web;
   a step of forming a pad of the absorbent sanitary article;
   a step of applying the pad to the frame by applying the pad to the first composite web;
   the step of forming the pad comprising:
      a step of making an absorbent core, comprising:
         a step of making a second composite web advancing along a feed direction; and
         a step of cutting the second composite web into a plurality of first lengths of absorbent core;
      a step of shaping the absorbent core, comprising:
         a step of preparing a succession of hollows in the second composite web, each of the succession of hollows being made by removing a corresponding portion of the second composite web before applying the pad on the first composite web;
   wherein the step of forming the pad further comprises a step of covering the absorbent core with an outer cover, the pad comprising the absorbent core and the outer cover;
   wherein the step of covering the absorbent core comprises a step of making a third composite web comprising the plurality of first lengths of absorbent core, the plurality of first lengths of absorbent core defining an intermediate layer of the third composite web.

2. The process according to claim 1, wherein the step of cutting the second composite web into the plurality of first lengths of absorbent core includes cutting the second composite web into the plurality of first lengths of absorbent core along a cutting direction transversal to the feed direction, each of the plurality of first lengths of absorbent core having a direction of extension parallel to the cutting direction.

3. The process according to claim 1, wherein each portion of the second composite web is picked up between a first and a second length of the second composite web, each corresponding to adjacent ones of the plurality of first lengths of absorbent core.

4. The process according to claim 1, wherein the step of making the second composite web further comprises:
   a step of feeding a first supporting web;
   a step of placing on the first supporting web at least one spread of an absorbent material;
   a step of positioning the at least one spread of the absorbent material on the first supporting web according to a predetermined model;
   a step of applying a second web on the first supporting web;
   a step of joining the first supporting web to the second web,
   the first supporting web, the at least one spread of the absorbent material and the second web defining the second composite web.

5. The process according to claim 4, wherein the predetermined model comprises providing that the second composite web is free from absorbent material at at least one area chosen from 1) the corresponding portion of the second composite web prior to removal and 2) an area along a cutting direction between adjacent ones of the plurality of first lengths of absorbent core.

6. The process according to claim 4, wherein the step of making a second composite web comprises a step of applying adhesive on at least one chosen from the first supporting web and the second web.

7. The method according to claim 1, and further comprising a step of applying the corresponding portion of the second composite web onto the second composite web on a length of the second composite web corresponding to a relative length.

8. The process according to claim 1, wherein the step of making the third composite web comprises:
   a step of feeding a third supporting web;
   a step of positioning a succession of the plurality of first lengths of absorbent core on the third supporting web, the plurality of first lengths of absorbent core being positioned on the third supporting web with the direction of main extension being transversal to the feed direction;
   a step of applying a fourth web on the plurality of first lengths of absorbent core and on the third supporting web;
   a step of joining the fourth web to at least the third supporting web,
   the third supporting web, the plurality of first lengths of absorbent core and the fourth web defining the third composite web.

9. The process according to claim 1, wherein the step of forming the pad comprises a step of shaping the pad, comprising:
   a step of preparing a succession of hollows in the third composite web, each hollow of the succession of hollows in the third composite web being made by removing a corresponding portion of the third composite web before applying the pad on the first composite web.

10. The process according to claim 9, wherein the step of forming the pad comprises a step of cutting the third composite web into a plurality of second sections according to a cutting direction transversal to the feed direction, each of the plurality of second sections having a direction of main extension parallel to the cutting direction.

11. The process according to claim 10, wherein the step of forming the pad comprises a step of applying on the third composite web the portions of the third composite web, each portion of the third composite web being positioned on a length of the third composite web corresponding to one of the plurality of second sections.

* * * * *